(12) United States Patent
Targotay et al.

(10) Patent No.: US 6,712,023 B2
(45) Date of Patent: Mar. 30, 2004

(54) CULTURE OF SESSILE MARINE ANIMALS

(76) Inventors: Bullent Kukurtcu Targotay, Calle de la Calera 3 Pligono Industrial de Tres Cantos, Madrid, E-28760 (ES); Santiago Naranjo Lozano, Calle de la Calera 3 Pligono Industrial de Tres Cantos, Madrid, E-28760 (ES); Carlos Barbero Garcia, Calle de la Calera 3 Pligono Industrial de Tres Cantos, Madrid, E-28760 (ES); Silvia Martin Benitez, Calle de la Calera 3 Pligono Industrial de Tres Cantos, Madrid, E-28760 (ES)

(*) Notice: Subject to any disclaimer, the term of this patent is extended or adjusted under 35 U.S.C. 154(b) by 0 days.

(21) Appl. No.: 10/355,500

(22) Filed: Jan. 31, 2003

(65) Prior Publication Data

US 2003/0111020 A1 Jun. 19, 2003

Related U.S. Application Data

(62) Division of application No. 09/674,796, filed as application No. PCT/GB99/01402 on May 5, 1999.

(30) Foreign Application Priority Data

May 5, 1998 (GB) .............................................. 9809588
Mar. 4, 1999 (GB) .............................................. 9905018
Mar. 4, 1999 (GB) .............................................. 9905021

(51) Int. Cl.⁷ .............................................. A01K 61/00
(52) U.S. Cl. ...................................... 119/208; 424/520
(58) Field of Search .......................... 119/208; 424/520, 424/547, 538

(56) References Cited

U.S. PATENT DOCUMENTS 3,779,209 A * 12/1973 Budge et al. ................ 119/240
5,089,273 A * 2/1992 Rinehart et al. ............. 424/520
5,628,280 A * 5/1997 Ericsson ...................... 119/239

FOREIGN PATENT DOCUMENTS

| EP | 0 860 111 A2 | 8/1998 |
| EP | 0 860 111 B1 | 8/2000 |
| FR | 2 617 373 A  | 4/1988 |

* cited by examiner

*Primary Examiner*—Charles T. Jordan
*Assistant Examiner*—Judith A. Nelson

(57) ABSTRACT

Sessile marine organisms are a source of many marine pharmaceuticals. A method of producing such a marine pharmaceutical is provided which involves positioning a plurality of like substrates in sea water, growing the organism on the plurality of substrates, harvesting the grown organism, and extracting the pharmaceutical from the harvested organism.

20 Claims, 5 Drawing Sheets

CULTURE OF SESSILE MARINE ANIMALS

CROSS-REFERENCE TO RELATED APPLICATIONS

This application is a divisional of copending application Ser. No. 09/674,796, filed May 29, 2001, now U.S. Pat. No. 6,544,560 which application was a 35 U.S.C. §371 National Phase filing of PCT Application No. PCT/GB99/01402 filed May 05, 1999, which application claimed priority under the following commonly owned British Patent Applications-Nos. 9809588.8, filed May 05, 1998, 9905018.9, filed Mar. 04, 1999, and 9905021.3, filed Mar. 04, 1999. The PCT application designated the United States and was published in the English language on Nov. 11, 1999 as WO 99/56535.

The present invention relates to the culture of sessile marine animals for extraction of marine pharmaceuticals. In particular, the present invention relates to methods and devices for the culture of marine organisms known as tunicates.

BACKGROUND OF THE INVENTION

Over the past years, a systematic screening of many kinds of marine organisms has been undertaken to discover natural compounds that might have pharmacological uses. Sessile marine invertebrates have been shown to be worthwhile sources of potentially useful natural products. Among these invertebrates, tunicates or ascidians (Tunicata, Ascidiacea) have turned out to be especially interesting as sources for such natural products. Research in various places has shown that several compounds isolated from tunicates, principally the ecteinascidins and didemnins, have a potential for therapy of human cancers.

Thus, for example, extraction of the tunicate *Ecteinascidia turbinata* has yielded ecteinascidin 743 and other antitumour ecteinascidin compounds, while extraction of the tunicate *Aplidium albicans* gives dehydrodidemnin B and other antitumour didemnin compounds. Likewise, many active compounds have been isolated from other sessile marine organisms, notably from sponges. Many of these compounds extracted from tunicates, sponges and other such organisms have a complex structure which makes chemical synthesis difficult.

Thus, for ecteinascidin 743 and many other interesting compounds, it remains a matter of collecting the organism in bulk from nature, for subsequent isolation of the desired active compound. *Ecteinascidia turbinata* (Herdman, 1880 1 Ascidiacea, Perophoridae), is a colonial ascidian of transparent tunic and usually bright orange colour. A colony consists of a dense group or cluster of elongated, somewhat club-shaped zooids, which are connected at their bases by a network of stolons that adheres to the surface of the object on which the colony grows. The colonies normally live in shallow water (0 to 15 m) and in lagoons, growing on red mangrove roots, rocks, shells, turtle grass, bottom sand or on plants such as Caulerpa or Posidonia species. It is common and widely distributed in mangroves areas of the Caribbean Sea and the Mediterranean Sea. *E. turbinata* reproduces by both a sexual cycle, in which eggs are hatched internally within a brood pouch and larvae are released when a zooid reaches maturation or asexually, by budding from the stolon or base. *Ecteinascidia turbinata* is currently collected in the Caribbean from underwater mangrove roots, where it occurs in the colonies. Diving is not without difficulties, and finding the colonies among the tangled roots presents further problems. Moreover, the collecting must be done in a sustainable manner.

Accordingly, development of novel drugs from these sources has been hindered by the fact that these animals are not abundant enough in nature and sustainable collection of sufficient mass to provide the amounts needed for manufacturing of their active components as drugs is difficult.

OBJECT OF THE INVENTION

The present invention is concerned with the provision of methods and devices for culture of tunicates and other sessile marine organisms. In particular, the present invention is directed at the production by farming of *Ecteinascidia turbinata*.

SUMMARY OF THE INVENTION

The present invention provides a method of producing a marine pharmaceutical by extraction from a sessile marine organism, which method comprises positioning a plurality of like substrates in sea water, growing the organism on the plurality of substrates, harvesting the grown organism, and extracting the pharmaceutical from the harvested organism.

In a related aspect, the present invention provides a method of farming a sessile marine organism intended for extraction of a marine pharmaceutical, which method comprises positioning a plurality of like substrates in sea water, allowing larvae from a colony of the organism to seed the substrates, growing the organism on the plurality of substrates, and harvesting the grown organism.

In another related aspect, the present invention provides a method of farming a sessile marine organism intended for extraction of a marine pharmaceutical, which method comprises positioning a plurality of like substrates in sea water, transplanting the organism onto the substrates, growing the organism on the plurality of substrates, and harvesting the grown organism.

Preferred Embodiments

We prefer that the marine organism is *Ecteinascidia turbinata* and the marine pharmaceutical is an ecteinascidin compound, particularly ecteinascidin 743. In another preferred embodiment, the marine organism is *Aplidium albicans*, and the marine pharmaceutical is a didemnin compound, particularly dehydrodidemnin B.

This invention provides a device and a method, which allows for monoculture of sessile marine animals, in particular of tunicates such as *E. turbinata*, in clean waters adjacent to or at a distance from their native locations, and their harvesting in amounts sufficient for industrial production of drugs from their extracts. In some versions, the invention is particularly adapted for application in areas of Mediterranean coastal lagoons, harbour areas, or in appropriately constructed tanks or canals, while in other versions it is particularly suited for use in Caribbean waters, notably Caribbean mangrove swamp, keys and canals, harbour areas, or in an appropriately constructed tanks growing on red mangrove roots, rocks, shells, turtle grass, bottom sand or on plants.

In the farming methods of this invention, one aspect involves transplanting the organism onto the substrates which then grow for harvesting. In one embodiment, individual organisms are transplanted onto the substrates. Alternatively, for example with sponges, fragments of organisms are transplanted onto the substrates.

For seeding by implants, small pieces (say about 20 gr.) cut off from young, growing colonies are transported to the device and preferably placed into support baskets or boxes or affixed to the holes of a net or to the spaces between the individual ropes or rods of the device. Fixation can be achieved if needed, by using lengths of string, rubber, or any other method that maintains contact between the stolon of the colony and the device surface. Asexual growth of the organisms gives rise to net increase of mass of tunicates under appropriate water conditions.

Another aspect of the farming method of this invention involves allowing larvae from a colony of the organism to seed the substrates which then grow for harvesting. In one embodiment, the substrates are placed adjacent the colony. Alternatively, at least one collector is placed adjacent the colony to collect larvae, and then larvae on the collector are subsequently employed to seed the substrates. In this alternative, the substrates can be in the general locality of the colony so that local handling of the collector with larvae is all that is needed, or the substrates can be remote from the colony, so that the collectors with larvae are transported to be adjacent the substrates.

For this aspect involving the use of collectors, the present invention further involves a method of harvesting tunicates, wherein a multiplicity of larval collectors are positioned in the vicinity of tunicate colonies, and larvae released from the colonies are allowed to collect on the larval collectors. The loaded collectors can then be left in position for the larvae to mature, or transferred to a fresh area for the larvae to mature.

The present invention also provides larval collectors each comprising a support which can be secured to a mangrove root at a tunicate colony, with one or more larval substrates for receiving larvae from the colony. The collector of this invention preferably comprises a support with elongate cords or other form of substrate extending therefrom to mimic mangrove roots suitable for colonisation by the larvae. The support is preferably generally circular, with the substrate at the periphery. The support suitably has a central aperture defined by the inner ends of inwardly extending flexible, fingers. At least one slot usually leads from the periphery of the support to the aperture. The collector is typically made up of one support and 4 to 8 elongate substrates, though a support can be provided at each end, particularly where the substrates lack rigidity and the root is not vertical.

The method then involves flexing open the support along the slot to allow the root to pass to the central aperture. The inner ends of the fingers can be adjusted and moved as necessary to engage the root without damaging it, and hold the support in place. Care is taken to ensure that the cords hang freely for receiving the larvae.

In one variation of the present invention, the support floats with the larval substrates hanging down in the water, if necessary with some weights. The support is preferably tethered to the mangrove plant or some other suitable fixing position.

For seeding by larval capture, adult colonies are brought in proximity to the device or vice versa, and the swimming larvae emitted as a result of the sexual cycle of these organisms are allowed to affix themselves. There they take hold, and differentiate into sessile adults which in turn grow into larger colonies.

After transplanting or seeding, the implants or larvae are allowed to grow and form colonies while submerged in clean sea water, natural or artificial, which provide a continuously renewable source of nutrients such as natural plankton or micro-organism contained in sea water. When an appropriate size is reached, the colonies can be harvested.

A fraction of the initially seed colonies or the grown colonies may be used to provide seed material for the next harvest, while the rest of the growth will be collected and stored appropriately.

For harvesting, colonies are cleaned of sediment by means of streams of water, extraneous organisms removed manually. Harvesting of the tunicate colonies after the growth period is achieved either manually by divers or by removing the device from the anchorage and hauling it on board a suitable vessel and the tunicates harvested by separating them from the support rods or mesh. Immediately afterwards, the tunicate can be stored by freezing in plastic bags or any other convenient means.

The present invention also provides devices for growth of sessile marine organisms comprising a plurality of substrates, preferably including vertically extending substrates.

A particularly preferred device for seeding the tunicates and allowing them to grow and increase in mass provided by the present invention consists essentially of an attachment and growth structure and, when necessary, a support system. The attachment and growth structure allows for direct fixing or attachment of seeding fragments or implants of the organism being cultured, while the support system keeps the attachment structure in place. Fragments of tunicate colonies (juvenile and small) are implanted manually or captured onto the support structure, using an elastic band or similar when necessary, and are allowed to grow until they reach an appropriate size for harvesting. The device can be employed as a submerged structure maintained between bottom anchorage and floating device or between sides of natural or artificial basin as means to attach the direct fixing substrates. Floating raft-like frames or platforms can also be employed to attach the direct fixing substrates.

Thus according to the present invention, there is also provided

A device for growing sessile marine organisms on substrates, comprising arrays of substrates forming an attachment and growth structure secured to a support flotation system provided with an anchoring system or a mooring system.

The growing device has an attachment and growth structure and a support system which can be assembled from:

Attachment and Growth Structure (1) A substrate of ropes, cables, meshes, nets, rods, planks, strips, bars, fillets, sticks, cages, or baskets made of materials compatible with sea water, such as non-toxic plastic or corrosion-resistant metal, wood, or synthetic materials, kept tort by attachment to an anchorage system.
(2) Parallel lines of sea water resistant ropes or strips parallel to the bottom of a sandy coastal area running between firmly set anchoring supports.
(3) Support lines of ropes, cables or chains onto which baskets, cages or perforated boxes, are deployed at intervals. The baskets, cages or perforated boxes can be closed so as to trap seed fragments of tunicate colonies or other organisms.

The free spaces or holes between contiguous rods or cables of the mesh or netting allow free passage of water and space for attachment and growth of the tunicate implants. Perforations on the baskets or boxes allow free passage of water, but contain initial seed implants.

Support System

When the meshwork used for attachment and growth is rigid enough, additional anchorage to bottom-lying heavy weights or sides of culture tanks is sufficient for support. When necessary, such as in mariculture applications, an anchorage system is provided by means of ropes, rods or cables stretched taught between bottom lying heavy weights and high buoyancy floats on the surface of the water. Maintenance of the whole device submerged and outstretched perpendicularly to the water surface is insured by attachment to the anchorage rods, ropes, cables or chains at each end of the support structure. When meshwork or netting is used, additional smaller floats or buoys can be used at regular intervals on the upper side of the mesh, to keep it unfolded and stretched out at all times. Additional anchorage at intervals to regularly spaced bottom weights is used to counter the additional floats or buoys. Alternatively, if canals or tanks are used, the whole support system can be fixed to the sides of the channel or the walls of the tank by using a rigid support frame of metal, wood or plastic. When baskets, perforated boxes or cages are used, the support frame may consist of one or two long lines of rope, cable or chain stretched out between anchor rods firmly affixed into the sea bottom or to the growth tanks.

In a preferred embodiment, a mesh or thick net of rope or other material such as high density polyethylene is used for attachment and growth in which the holes or spaces are between 2 and 20 mm. This mesh or net is assembled onto, and held unfolded by, an anchorage-fixation system, comprising of cables stretched out between a heavy anchoring weights and buoys. High buoyancy (suitably 20 to 50 kg lift) air buoys are attached to one end of each cable, while the other end is fixed to heavy weights (tared heavier than the buoys' lift) at the bottom so that the whole structure rests essentially perpendicular to the water surface. The whole attachment meshwork is affixed to the anchor system insuring it stays outstretched and does not float away from the farming zone with the currents.

In an alternative embodiment, the frame structure consists of a rectangular panel formed by two parallel arrays or set of wooden or plastic rods or strips, firmly affixed to each other at an angle by use of ropes, screws or other means so as to make it rigid enough to be self supporting. Alternatively, it can be affixed to the bottom using rigid frameworks of light metal, wood or plastic.

A preferred device is employed in a method of growing *Ecteinascidia turbinata* by transplanting fragments of colonies of the organism to a substrate using as substrate and support a device essentially as described for example in FIG. 4 and comprising of lengths of an approximately 0.5 to 4 m wide plastic mesh with holes between 2 and 8 cm kept entirely submerged by anchorage to the bottom of a shallow coastal lagoon and held approximately vertically by floatation devices.

A device useful for seeding and growing sessile marine organisms, in particular tunicates such as *E. turbinata*, at sites close to or remote from natural colonies is also provided. This device consists essentially of an attachment and growth structure within a support-flotation frame, which is held by an anchor-fixation system and may have a shade attached to it.

The growing device consists essentially of:
a support frame and floatation structure,
attachment guides,
fixation and anchorage system and usually
a shade.

A device for growing sessile marine organisms on substrates, comprising arrays of vertically extending substrates each attached to a respective one of an array of horizontal attachment guides secured to and supported by a support flotation frame provided with an anchoring system or a mooring system, and optionally having a shade to reduce light incident on the substrates.
Support Frame and Floatation Structure This structure consists essentially of an internal perimeter support for the attachment rods and an external perimeter, which serves to attach the whole structure to the walls of a tank or a floatation-anchorage system for open sea applications. Both perimeters are formed by a set of wooden or plastic rods firmly affixed to each other by use of screws or other means so as to make it rigid enough to allow for support of the growth rods from it. The internal frame perimeter may be assembled in the same plane as the external one or may be held in a lower plane so that it is kept submerged in the water while the external frame remains on the surface, depending on the geometry of the floatation system, and other specific culture requirements.
Attachment Guides The internal part of the support frame serves as fixation for the "attachment guides" which are several parallel rods, strips, fillets or ropes of material compatible with &p sea water, such as jute, wood, corrosion-resistant metal or synthetic materials. These "attachment guides" affixed to the frame by means of hooks or similar fixations so that each end can be detached easily from the frame, forming a horizontal, parallel array and kept submerged close to the surface of the water by the internal part of the support frame.
Fixation and Anchorage System For mariculture applications, the whole device is set to float horizontally on the surface of the water. This may be achieved by attachment of low average density structures to the external perimeter areas of the frame structure. In this case the whole attachment frame is anchored to bottom lying heavy weights by means of ropes, chains or cables, such that it floats on the surface of the water but does not float away from the farming zone with the currents.

The device may also be adapted use in tanks or canals and fixed to the bottom or sides by means or any sufficiently firm fixation framework of light metal, wood or plastic. In a preferred embodiment of this invention, large enough pieces of a low average density polymeric material such as pre-expanded polyurethane are attached to the spaces between the rods forming each lateral pair of the support frame, so that the whole structure floats in the water.
Shade A covering material may be used to reduce total light incidence on the surface of the water immediately over the attachment rods in areas exposed to intense sunlight. In a preferred embodiment of this invention, a length of a sturdy cloth or dense mesh is used attached at each end to wooden or plastic rods (shade rods) in a way which allows easy removal of the shade for access to the growing culture from above.

A preferred device is employed in a method of capturing *Ecteinasicidia turbinata* larvae onto 0.2–2 m lengths of ropes or wooden rods using a device essentially as described for example in FIGS. 5, 6 and 7 comprising of a floating frame, approximately 1–2 m by 3–6 m with a shade onto which the ropes or wooden rods are affixed and maintained horizontally or vertically submerged in the water in proximity to colonies of the organism until larvae attach to them so that adult colonies can later be grown from these ropes or rods so seeded.

Another preferred device is employed in a method of growing *Ecteinascidia turbinata* by implanting fragments of colonies onto 0.2–2 m lengths of ropes or wooden rods using a device essentially as described for example in FIGS. 8, 9 and 10 comprising of a floating frame, approximately 1–2 m by 3–6 m with a shade from which the ropes or wooden rods with attached colonies can hang vertically submerged in water for growth of the organism.

EXAMPLES OF THE INVENTION

The present invention is exemplified by the embodiments shown in the accompanying drawings.

THE DRAWINGS

Figure 1:
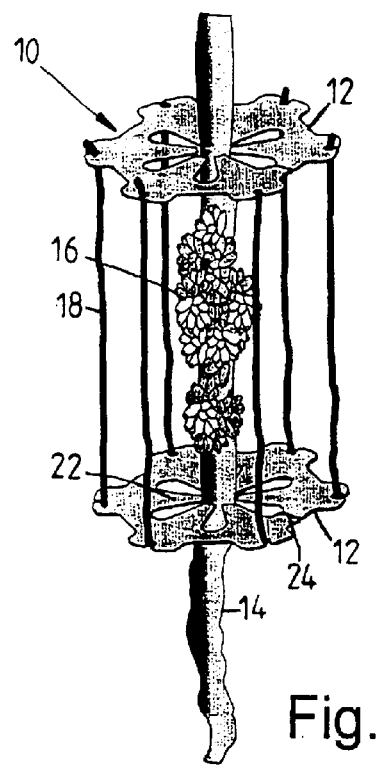
FIG. 1 is a perspective view of a larval collector of this invention in position around a tunicate colony.

Referring initially to FIG. 1, the larval collector 10 of this invention has two polypropylene supports 12 which can be secured to a mangrove root 14 at a tunicate colony 16. Six plastic cords 18 of polypropylene, nylon or polyethylene and about 60 cm in length form larval substrates for receiving larvae from the colony.

In the collector 10 of FIG. 1, there are supports 12 at opposite ends, though initial experience suggests that only the upper support is needed for a generally vertical root 14. Each support is generally circular, and as may also be seen in FIG. 2, there is a central aperture 20 defined by the inner ends 21 of inwardly extending flexible fingers 22. The fingers can have a narrowed section 23 to facilitate flexing. A slot 24 leads from the periphery of the support to the aperture 20.

In use, the assembled collector is taken underwater to a mangrove root 14 with a tunicate colony 16. The support is flexed open along the slot 24 to allow the root to pass to the central aperture 20. The inner ends 21 of the fingers 22 can be adjusted and forced as necessary to engage the root and hold the support in place.

After the larvae have migrated to the plastic cords 18, the loaded collectors 10 can then be left in position for the larvae to mature, to grow to give new colonies 26 indicated by the dashed lines. Alternatively, the loaded collectors can be transferred to a fresh area for the larvae to mature elsewhere. In particular, each loaded substrate can form the basis for a new colony in a new area, which in turn can then be subjected to larval collection using the present invention.

Figure 3:
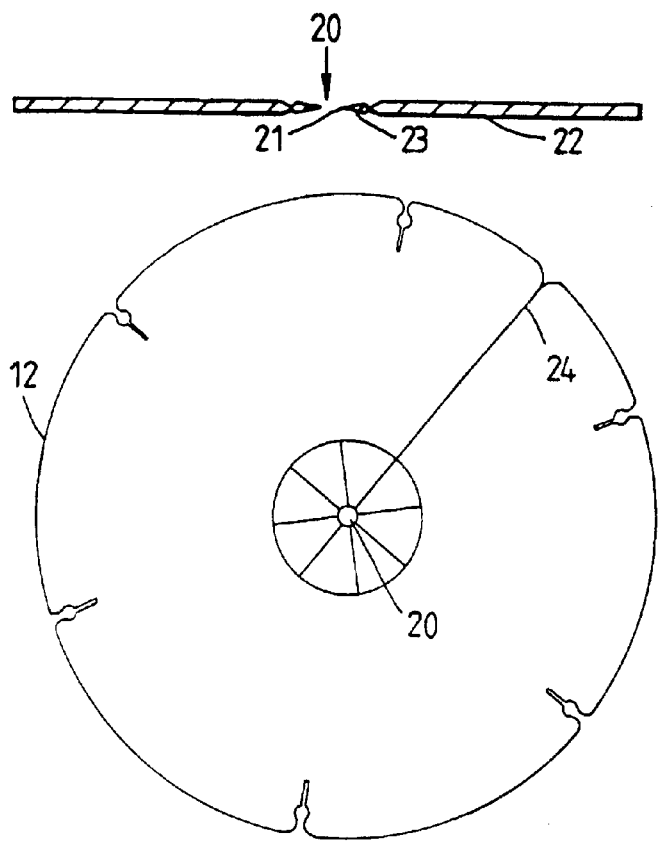
FIG. 3 is a view from above of a different support for a larval collector of this invention, together with a horizontal cross-section of the support.

FIG. 3 shows a different support for a larval collector with a horizontal cross-section of the support. The measurements of the support of FIG. 3 are as follows:

| | |
|---|---|
| Diameter of the support | 250 mm. |
| Diameter of the central circle | 60 mm. |
| Diameter of the circle described by the tip (end) of the wings | 7 mm. |
| Diameter of the circular slots for the string passing | 6 mm. |
| Width of the neck of the circular slots | 4 mm. |
| Width of the opening to the circular slots for the string passing | 2 mm. |
| Length of the opening to the circular slots for the string passing | 10 mm |
| Width of the opening to the central circle of the support | 1.5 mm. |
| Thickness of the support | 3.5 mm. |

In the case of the Caribbean tunicate *Ecteinascidia turbinata* the release of larvae occurs about 4 or 5 times a year. It is desirable to position the collectors in the light of the expected release times, and to then monitor the collectors at regular intervals.

By the use of the present invention, it becomes possible to envisage the large scale farming of tunicates, especially *Ecteinascidia turbinata*.

Figure 2:
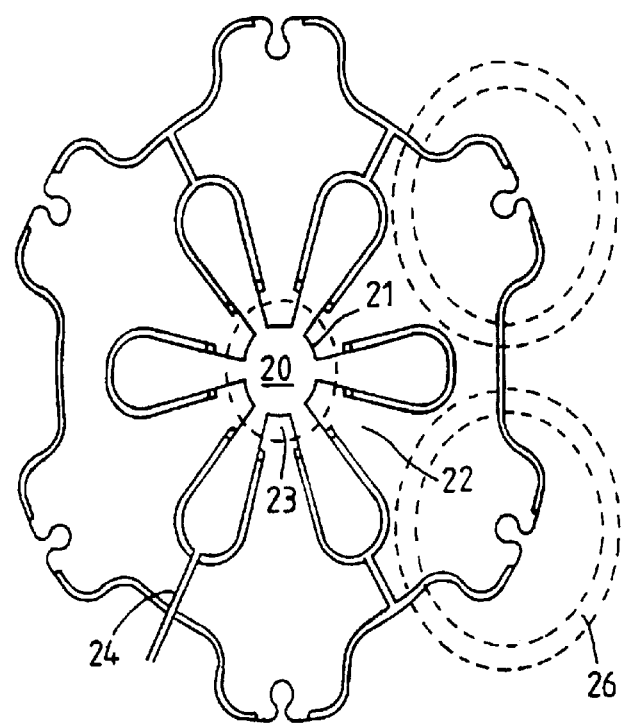
FIG. 2 is a view from above of a support for use in the larval collector of FIG. 1, together with a horizontal cross-section of the support.
Figure 4:
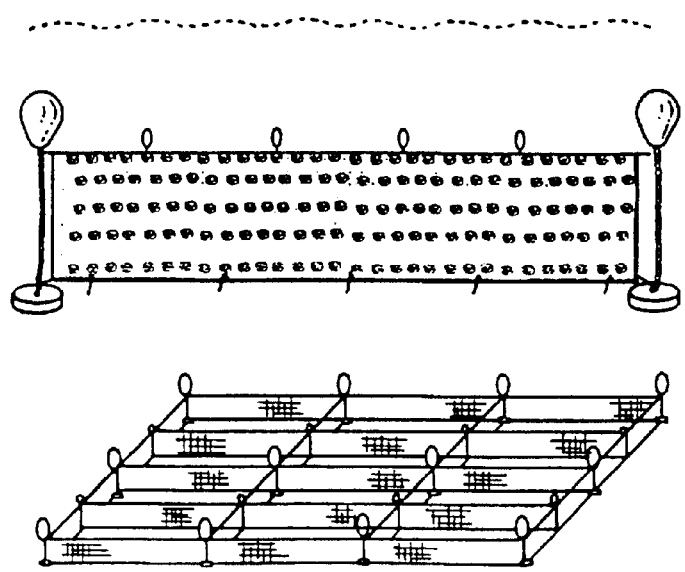
FIG. 4 is a growth device with meshwork attachment structures suited for use in the Mediterranean Sea.

Thus, with the embodiment of FIGS. 1 to 3, we provide an environmentally favourable method of farming for sustainable exploitation of the naturally occurring resource, that is a method of farming *Ecteinascidia turbinata* which comprises collecting the larvae on a substrate and allowing the larvae to grow to maturity. From the mature tunicates, or from their subsequent progeny, the desired compound such as ecteinascidin 743 can be isolated. The isolated compound is also part of the present invention Referring to FIG. 4, there is shown a growth device with meshwork attachment structures suited for use in the Mediterranean Sea. The substrate comprises a the meshwork which is anchored by heavy weights and buoyed by flotation buoys. FIG. 4A shows a single growth device, and FIG. 4B shows a grouping of multiple devices.

Figure 5:
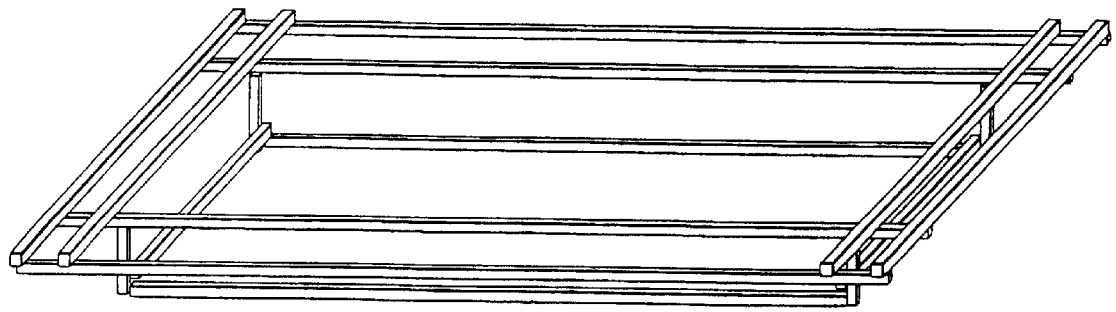
FIG. 5 shows a frame for larval capture.
Figure 6:
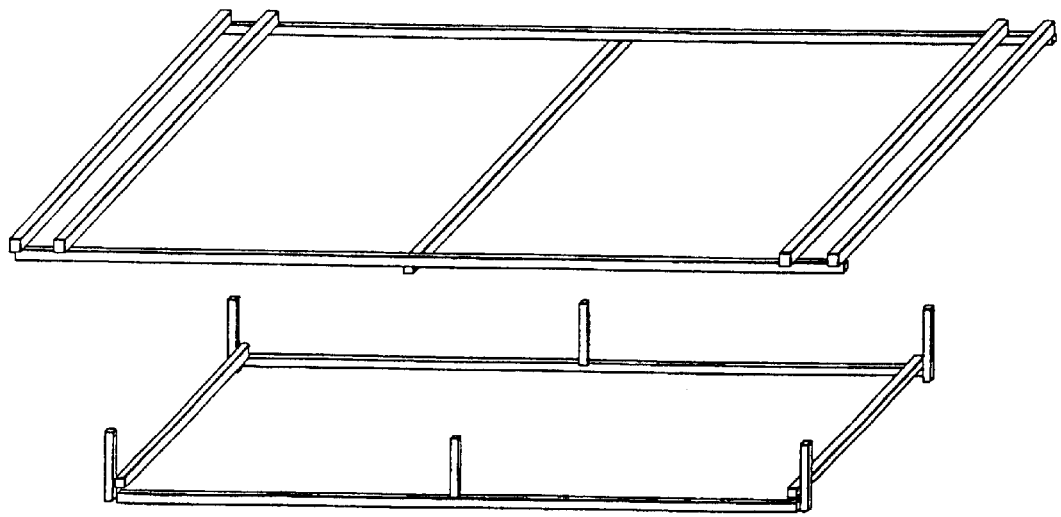
FIG. 6 is an exploded view of the frame of FIG. 5.
Figure 7:
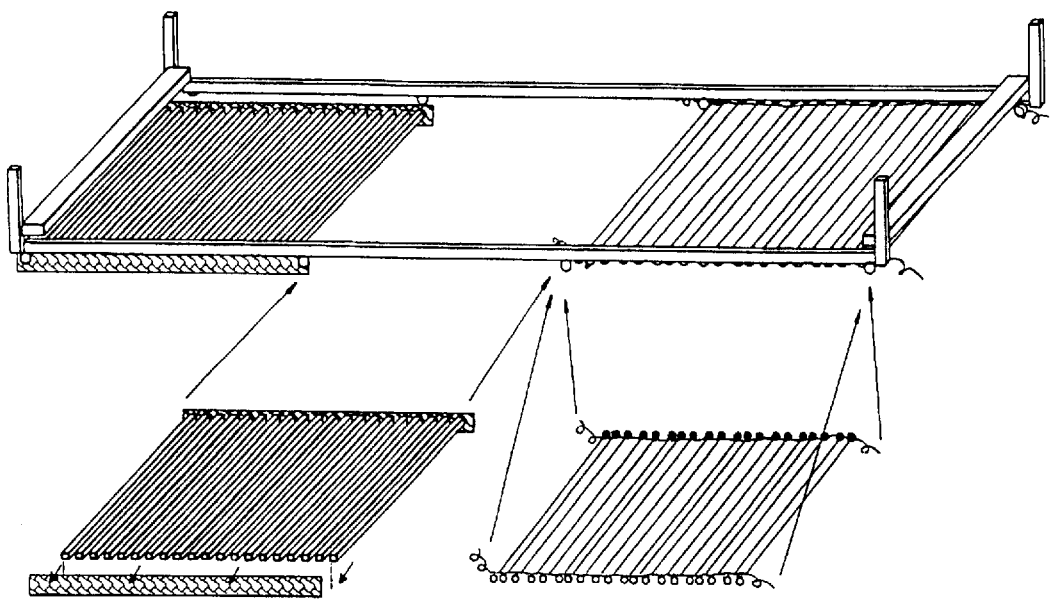
FIG. 7 is a detail of the underwater area, the collectors, of a frame for larval capture.
Figure 8:
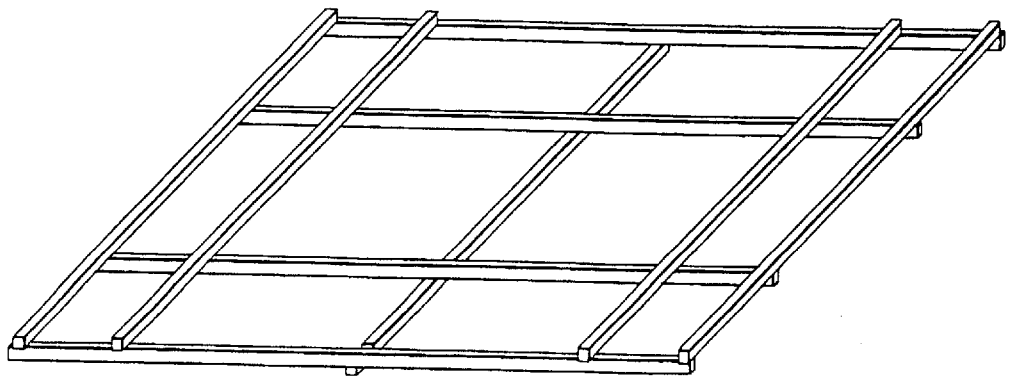
FIG. 8 is a frame for growth of tunicates.
Figure 9:
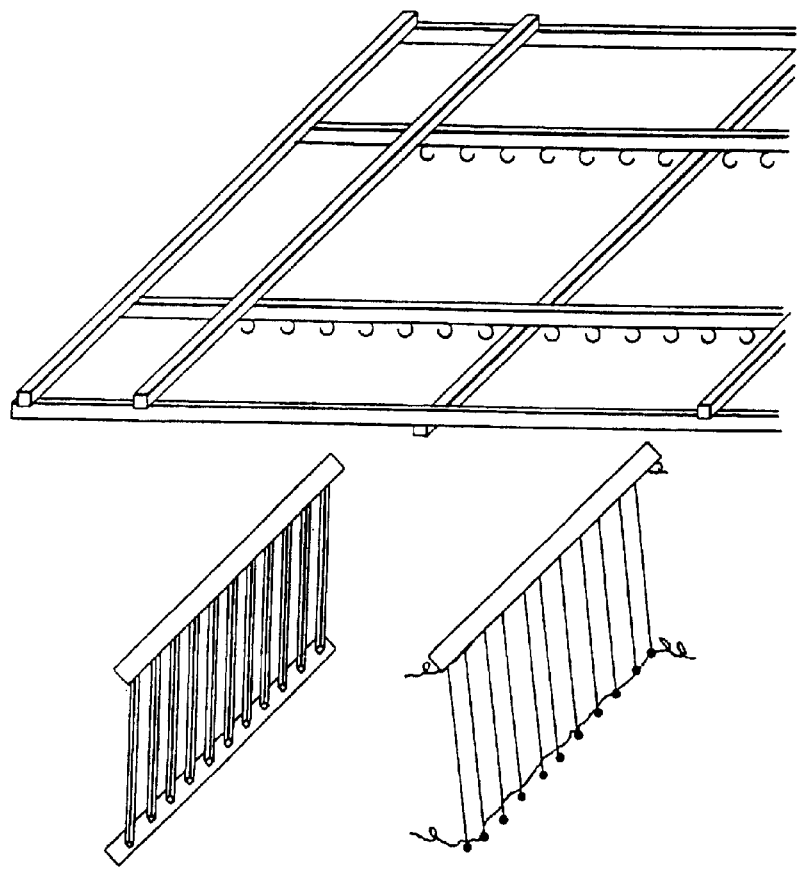
FIG. 9 is a detail of the frame of FIG. 8.
Figure 10:
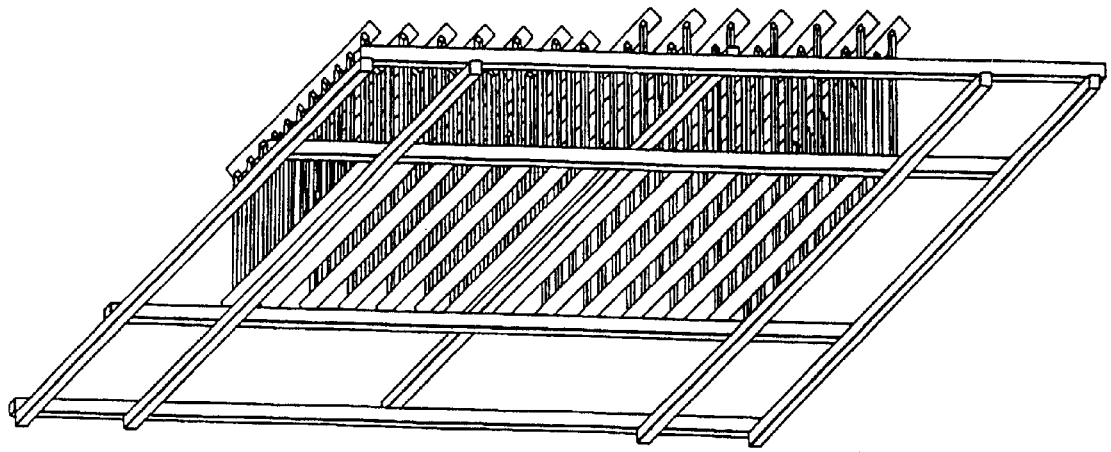
FIG. 10 is a detail of a growth unit.

A preferred embodiment of this invention useful for mariculture of tunicates in Caribbean mangrove coastal areas, in particular of *E. turbinata*, is shown in FIGS. 5 to 9. FIG. 5 shows a frame for larval capture. The external and internal perimeter are shown in FIG. 6. In FIG. 7 are alternative details using wooden rods or ropes for larval capture collectors. FIG. 8 depicts a frame for growth of tunicates. FIG. 9 shows alternatively attachment rods or attachment ropes in a detail of a frame for growth of tunicates. FIG. 10 shows attachment rods secured to support rods in a detail of the growth units.

For this application, frame structures are used comprising of rectangular arrays of 4 parallel pairs of wooden rods or polymeric plastic rods screwed together as depicted in the drawings. In this fashion, an internal rectangular space is left free for attachment of the growth rods. For applications of larval capture, a frame may be used in which the internal perimeter is positioned between 0 and 50 cm below the external one to insure the attachment rods are kept submerged appropriately. The attachment rods are constructed of wood, plastic tubing or ropes with appropriate fixtures at the ends to fit on hooks on the internal frame and placed horizontally within the internal frame. Growing tunicate colonies attached to an attachment guide or to a natural substrate are brought in proximity to the device and allowed to emit larvae. After a while, rods with larvae affixed are released from one end and transferred to a support frame for growth. For growth of preimplanted organisms, the internal perimeter may be in the same plane as the external one, and resting on the surface of the water horizontal support rods transverse the internal frame. Vertical attachment rods or ropes bearing either attached larvae or implanted tunicate colony fragments are placed hanging down from the horizontal ones to allow growth of the tunicates. The rods or ropes can be released at both ends in order to harvest the entire growth of tunicate. Pre-expanded polyurethane slabs are affixed to the space between the external and internal perimeter of the frame for floatation. The whole attachment frame is anchored to heavy weights by means of ropes.

The process followed for cultivation includes an initial seeding followed by a growing phase and harvest.

Adult tunicate colonies can be brought in proximity to the structure, and the larvae emitted as a result of the sexual cycle of these organisms are captured, or allowed to affix themselves to the rods of the structure, favourably when in horizontal position. Alternatively, ropes on which tunicate larvae have been similarly captured are attached to the rods of the support structure. There they take hold, and differentiate into sessile adults, which in turn grow into larger colonies.

Alternatively, for seeding by implants, small fragments (say about 20 gr.) cut off from growing organism such as sponges or tunicate colonies are transported to the attachment structure and affixed to the growth rods by means of rubber bands or any other method that maintains contact between the stolon of the colony and the attachment surface. Alternatively, ropes to which tunicate colony or sponge fragments have been similarly affixed are attached to the rods of the attachment structure. Asexual growth of the organisms gives rise to net mass increase.

Rods or ropes with larvae affixed or with fragments of live adult organism are allowed to adopt a vertical position in which larvae are allowed to grow and form colonies. Asexual growth of the organisms gives rise to net increase of mass of tunicates. A fraction of the colonies initially seeded may be used to provide seed material for the next harvest, while the rest of the growth will be collected and stored appropriately.

For harvesting, colonies are cleaned of sediment by means of streams of water, extraneous organisms removed manually if needed and the animals harvested by separating them from the attachment rods, and stored frozen as appropriate.

What is claimed is:

1. A method of farming a sessile marine organism intended for extraction of a marine pharmaceutical, which method comprises positioning a plurality of like substrates in sea water, allowing larvae from a colony of the organism to seed the substrates, growing the organism on the plurality of substrates, and harvesting the grown organism.

2. A method according to claim 1, wherein the substrated are placed adjacent the colony.

3. A method according to claim 1, wherein at least one collector comprising a support with substrates is placed adjacent the colony to collect larvae.

4. A method according to claim 3, wherein the collector is transferred to another site for growth of the organism.

5. A method of farming a sessile marine organism intended for extraction of a marine pharmaceutical, which method comprises positioning a plurality of like substrates in sea water, transplanting the organism onto the substrates, growing the organism on the plurality of substrates, and harvesting the grown organism.

6. A method according to claim 5, wherein individual organisms are transplanted onto the substrates.

7. A method according to claim 5, wherein fragments of organisms are transplanted onto the substrates.

8. A method according to any one of claims 5 to 7, wherein the substrates are provided by cables, ropes, meshes, nets, rods, planks, cages, and baskets for direct fixing of the organism.

9. A method according to any one of claims 5 to 8, wherein submerged structures comprising the substrates are maintained between bottom anchorage devices and flotation devices.

10. A method according to any one of claims 5 to 8, wherein submerged structures comprising the substrates are maintained between sides of a natural or artificial basin.

11. A device for culturing of sessile marine organisms which comprises a support frame and flotation structure, attachment guides, substrates for securing to the attachment guides, a fixation and anchorage system, and optionally a shade.

12. A device for growing sessile marine organisms on substrates, comprising arrays of vertically extending substrates each attached to a respective one of an array of horizontal attachment guides secured to and supported by a support flotation frame provided with an anchoring system or a mooring system, and optionally having a shade to reduce light incident on the substrates.

13. A device for growing sessile marine organisms on substrates, comprising arrays of substrates forming an attachment and growth structure secured to a support flotation system provided with an anchoring system or a mooring system.

14. A method of growing *Ecteinascidia turbinata* by transplanting fragments of colonies of the organism to a substrate using as substrate and support a device comprising of lengths of an approximately 0.5 to 4 m wide plastic mesh with holes between 2 and 8 cm kept entirely submerged by anchorage to the bottom of a shallow coastal lagoon and held approximately vertically by flotation devices.

15. A method of capturing *Ecteinascidia turbinata* larvae onto 0.2–2 m lengths of ropes or wooden rods using a device comprising of a flotation frame, approximately 1–2 m by 3–6 m with a shade onto which the ropes or wooden rods are affixed and maintained horizontally or vertically submerged in the water in proximity to colonies of the organism until larvae attach to them so that adult colonies can later be grown from these ropes or rods so seeded.

16. A method of growing *Ecteinascidia turbinata* by implanting fragments of colonies onto 0.2–2 m lengths of ropes or wooden rods using a device comprising of a floating frame approximately 1–2 m by 3–6 m with a shade from which the ropes or wooden rods with attached colonies can hang vertically submerged in water for growth of the organism.

17. A method of farming a marine sessile organism that is *Ecteinascidia turbinata* intended for extraction of a marine pharmaceutical, which method comprises positioning a plurality of like substrates in sea water, seeding the substrates with *Ecteinascidia turbinata* organism, growing the organism on the plurality of substrates and harvesting the grown organism.

18. The method of claim 17, wherein said seeding of substrates is carried out by contacting larvae of said organism *Ecteinascidia turbinata* with said substrates.

19. The method of claim 17, wherein said seeding of substrates is carried out by transplanting said *Ecteinascidia turbinata* organism on to said substrates.

20. The method of claim 19, wherein said seeding of substrates is carried out by transplanting fragments of colonies of said *Ecteinascidia turbinata* organism on to said substrates.

* * * * *